United States Patent [19]

Muto et al.

[11] 4,419,889
[45] Dec. 13, 1983

[54] MOISTURE SENSITIVE DEVICE

[75] Inventors: Katsutoshi Muto; Takao Sawada; Yoshiharu Komine, all of Hyogo, Japan

[73] Assignee: Mitsubishi Denki Kabushiki Kaisha, Tokyo, Japan

[21] Appl. No.: 248,374

[22] Filed: Mar. 27, 1981

[51] Int. Cl.³ .............................................. G01W 1/00
[52] U.S. Cl. .................................... 73/336.5; 338/35; 252/408.1
[58] Field of Search ................ 73/336.5, 335; 338/35; 324/65 R

[56]      References Cited
U.S. PATENT DOCUMENTS

| 4,080,564 | 3/1978 | Nitta et al. | 324/65 R |
| 4,321,577 | 3/1982 | Carlson | 338/35 |
| 4,326,414 | 4/1982 | Terada et al. | 73/336.5 |

OTHER PUBLICATIONS

Nitta and Hayakawa, "Ceramic Humidity Sensors", *IEEE Transactions on Components, Hybrids, and Manufacturing Technology*, vol. CHMT-3, No. 2, Jun. 1980, pp. 237-243.

*Primary Examiner*—Gerald Goldberg
*Assistant Examiner*—John E. Chapman, Jr.
*Attorney, Agent, or Firm*—Sughrue, Mion, Zinn, Macpeak and Seas

[57]              ABSTRACT

A moisture sensitive device is disclosed which comprises a moisture sensitive element including a material comprising a hydroxyapatite, i.e. $M_{10}(PO_4)_6(OH)_2$, wherein M is at least one member selected from the group consisting of Sr, Ca and Ba, at least two electrodes formed on the moisture sensitive element, with the electrodes being separated by the element, and electrical leads connected to each of the electrodes.

15 Claims, 16 Drawing Figures

— BEFORE CONTAMINATION BY SALAD OIL MISTS
—·—·— AFTER CONTAMINATION BY SALAD OIL MISTS

TIO BASE ---------

APATITE BASE ———

| NO. | TIME AFTER HEATING |
|-----|--------------------|
| 1   | 5 MINUTES          |
| 2   | 1 DAY              |
| 3   | 8 DAYS             |
| 4   | 22 DAYS            |
| 4'  | 31 DAYS            |

MOISTURE SENSITIVE DEVICE

BACKGROUND OF THE INVENTION

This invention relates to a moisture sensitive device that measures relative humidity using the proportional relationship between relative humidity and electrical resistivity. More particularly, the invention relates to a new moisture sensitive device that is useful, e.g., to indicate when cooking has been completed in a microcomputer-controlled microwave oven by measuring the the humidity in the oven, or to control the amount of steam supplied by a humidifier in an FF (forced flue) heater.

The recent advance of electronic control technology has been remarkable, and many home appliances, such as microwave ovens, FF heaters, and air conditioners are now operated under the control of a microcomputer. Of course it would be desirable that if a microcomputer is used at all, it should be able to make decisions and carry out sophisticated job functions other than just telling time (i.e., a timer's function) and executing a prestored program, but to do this, various types of information must be gathered and supplied to the microcomputer and, particularly, a moisture sensitive device is necessary for gathering information on humidity.

Moisture sensitive devices are known that measure relative humidity by converting relative humidity into electrical resistivity which is proportional to relative humidity. A conventional moisture sensitive device of this type uses a metal oxide (e.g., $Fe_2O_3$, $Al_2O_3$, or NiO) as a moisture sensitive element. However, a moisture sensitive device using such a metal oxide does not have a relative humidity versus electrical resistivity profile that satisfactorily meets all requirements for practical use. For instance, a moisture device using NiO is not very sensitive at a relative humidity lower than 60%, and those using $Fe_2O_3$ or $Al_2O_3$ have an undesirably high resistivity for some values of relative humidity. A moisture sensitive device using a material that consists mainly of lithium chloride is also well known, but since it is deliquescent, the salt may become liquid under high humidity conditions, rendering the device inoperable. Therefore improved moisture sensitive devices have been desired.

SUMMARY OF THE INVENTION

It is an object of this invention to overcome the deficiencies of conventional moisture sensitive devices.

Therefore in accordance with this invention, there is provided a moisture sensitive devices comprising a moisture sensitive element including a material comprising $M_{10}(PO_4)_6(OH)_2$, wherein M is at least one member selected from the group consisting of Sr, Ca, and Ba, at least two electrodes formed on said moisture sensitive element, with said electrodes being separated by said element, and an electrical lead connected to each of said electrodes. This device is capable of accurate measurement of relative humidity in a range of from 0 to 100%.

Other objects and advantages of this invention will be apparent from the following description of preferred embodiments and the accompanying drawings.

BRIEF DESCRIPTION OF THE DRAWINGS

FIGS. 5 to 10 are diagrams showing the characteristics of the moisture sensitive device according to a first embodiment of this invention, wherein FIG. 5 depicts a relative humidity versus electrical resistivity curve, FIG. 6 depicts a response speed curve, FIG. 7 depicts a temperature dependency curve, FIG. 8 depicts a resistance-to-contamination curve, FIG. 9 depicts a resistance-to-repeated-heating curve, and FIG. 10 depicts the time-dependent change in the relative humidity versus electrical resistivity profile;

DESCRIPTION OF PREFERRED EMBODIMENTS

A first embodiment of this invention is hereunder described by reference to FIGS. 1 to 10.

During an extensive period of study for a material for a moisture sensitive element that showed low electrical resistivity under various conditions of relative humidity, and which exhibited electrical resistivity that varied over a relative humidity range of from 0% to 100% greatly enough to achieve accurate measurement of relative humidity, hydroxyapatite was found to be of interest. having the formula $M_{10}(PO_4)_6(OH)_2$, wherein M is Ca, Ba, Sr, Mg, Na, etc., hydroxyapatite is known as the major inorganic component of structures such as animal bones and teeth, and, as is evidenced by the fact that fossils made thereof have been preserved for hundreds of millions of years, it is very stable. Interest in hydroxyapatite developed because the extensive research on moisture sensitive materials leading to the claimed invention had shown that it contains OH groups that display important moisture sensing properties, that is solubility in water is fairly small ($K_s = 10^{-115}$), that its particles have a large surface area (60–70 m²/g), that it can be produced from inexpensive materials, and that it is chemically stable.

Using hydroxyapatite, a moisture sensitive device was prepared in the following manner. As a starting material, $CaHPO_4$ and $CaCO_3$ having a purity of more than 99.9% were measured to provide the appropriate ratio of materials for a composition of $Ca_{10}(PO_4)(OH_2)$ to be formed, and mixed in a ball mill thoroughly. The mixture was put in a crucible and heated in an electric oven (using a conventional silico-unit heat element) in air at 600° C. for 10 hours. The heated mixture was ground into fine particles which were then placed in an aqueous solution of polyvinyl alcohol in a mortar, and the resulting slurry was subsequently treated to provide granules of uniform size. The granules were pressed into a disc (25 mm in diameter and 3 mm thick) at a pressure of 700 kg/cm² using a press moulding machine, and the disc was then fired in the electric oven in a steam atmosphere at 1000° C. The disc was then allowed to cool to room temperature. A powder X-ray photograph of the resulting ceramic composition showed that $CaHPO_4$ reacted chemically with $CaCO_3$ to form a very stable hydroxyapatite, i.e., $Ca_{10}(PO_4)_6(OH)_2$, according to the reaction

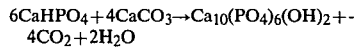

Figure 1:
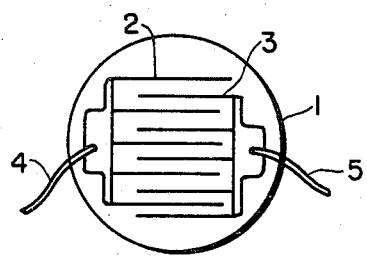
FIG. 1 is a schematic view showing the construction of a moisture sensitive device useful according to first and second embodiments of this invention described hereinafter.

The ceramic composition of the formula $Ca_{10}(PO_4)_6(OH)_2$ was formed into a moisture sensitive element represented at 1 in FIG. 1. One side of the element was polished with an abrasive of mesh 800, and two comb-like patterns of gold paste were printed on the polished surface by a screen mesh method, and fired in the electric oven in air at 800° C. to provide a pair of comb-shaped electrodes 2 and 3. The electrodes 2 and 3 were separated from each other by the hydroxyapatite material 1. The element was recovered from the oven and a moisture sensitive device was fabricated by soldering 90% platinum-rhodium leads 4 and 5 to the electrodes 2 and 3, respectively. An ohmmeter was connected between the leads 4 and 5, and the restivity across the comb electrodes 2 and 3 was measured by varying the relative humidity over a range of from 0% to 100% at 20° C. The results are depicted by the relative humidity versus electrical resistivity curve shown in FIG. 5. As one can easily see from the figure, the moisture sensitive device according to the first embodiment of this invention exhibited a substantially linear relative humidity versus electrical resistivity profile for a relative humidity range of from 0% to 100%, thus being able to achieve accurate measurement of relative humidity over a wide range.

The response characteristics of the moisture sensitive device according to this first embodiment of this invention were examined by varying the relative humidity at 20° C. from 1% to 51% (the process of adsorption) and by changing it from 94% to 51% (the process of desorption). The results are depicted by the relative humidity versus response time curve shown in FIG. 6. As seen from the figure, the time necessary for obtaining 90% of the required change in relative humidity was 2 seconds in the process of adsorption and 15 seconds in the process of desorption. This indicates that the time required for the device to respond to a change in relative humidity from 0 to 100% is much less than 100 seconds, which is sufficient for practical purposes.

The temperature-dependent change in the relative humidity versus electrical resistivity profile of the device was examined by varying the ambient temperature to 20° C., 40° C. and 60° C., respectively and changing the relative humidity in a range of from 0 to 100%. The results are depicted by the three curves shown in FIG. 7. As the figure shows, a temperature change of about 5° C. causes an error in relative humidity (RH) measurement of about 5% RH for a particular electrical resistivity, but since the moisture sensitive device contemplated by this invention is generally used at a temperature between 15° C. and 25° C., this amount of error will present no problem for practical purposes.

To check the resistance of the moisture sensitive device of the first embodiment of this invention against contaminants, the device was exposed to the mist of salad oil and the relative humidity of the mist was changed from 0 to 100%. The results are depicted by the electrical resistivity versus temperature curves shown in FIG. 8. As the figure shows, the device exhibited an increasing electrical resistivity in a salad oil mist, but upon heating to about 450° C., the performance of the device was restored in the initial level, and hence, the device was found to have a resistance to contamination that was satisfactory for practical purposes. Thus the moisture sensitive device of this invention can be cleaned of contaminants by raising the temperature to about 450° C. The resistance of the device to repeated heating was checked by repeating the heating of the device at 450° C. at intervals of 5 minutes in air. The results are depicted by the characteristic curves shown in FIG. 9 from which it can be seen that the device that had gone through 40,000 heatings was as sensitive to moisture as the unheated device. This is another indication of the practical value of the device of this invention.

Figure 10:
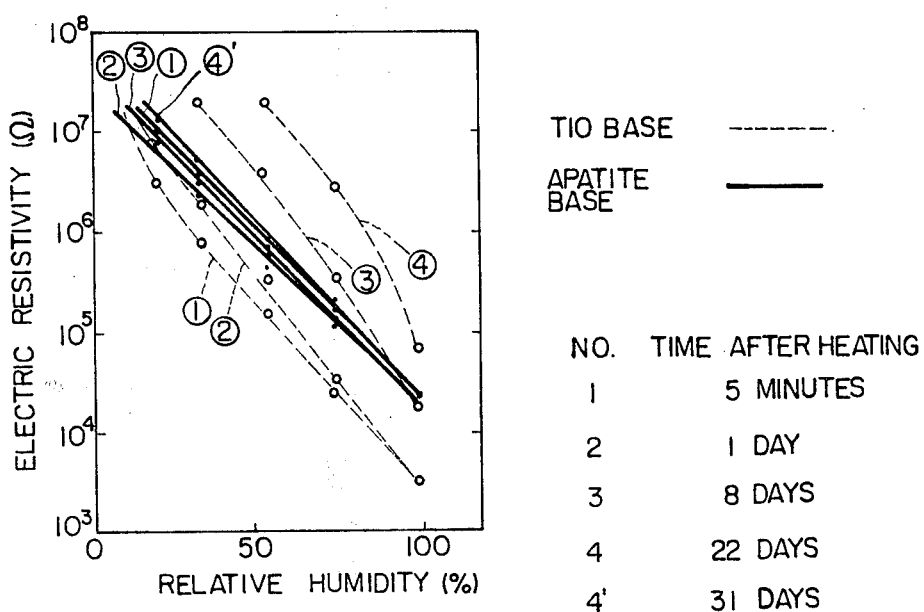

To check how the moisture sensitivity of the device according to the first embodiment of this invention changed with time after heating to 450° C., the heated device was allowed to stand in air together with the conventional $TiO_2$-base moisture sensitive device for a specified period of time. The results depicted in FIG. 10 show the relative humidity versus electrical resistivity characteristic curves for standing for periods of 5 minutes, 1 day, 8 days, 22 days and 31 days after heating. As is clear from the figure, the relative humidity versus electrical resistivity profile of the moisture sensitivity device of this invention remains substantially the same during standing for 30 days after heating.

In the embodiment described above, the starting material was $CaHPO_4$ and $CaCO_3$ having a purity of more than 99.9%, but a starting material of lower purity can be used if the impurities it contains so permit. It has also been found that the material for the moisture sensitive element 1 can also be prepared by synthesis in an aqueous solution or any other method well known in the ceramic industry.

Figure 2:
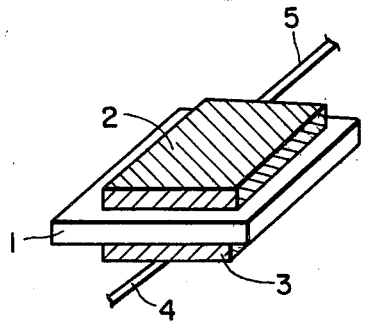
FIG. 2 is a perspective view showing the construction of another moisture sensitive device useful according to the first and second embodiments of this invention.
Figure 3:
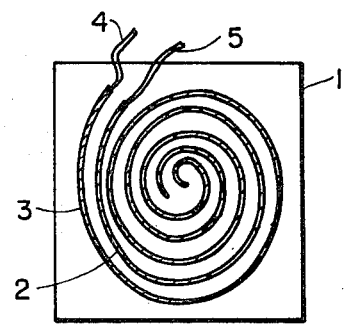
FIG. 3 is a schematic view showing the construction of still another moisture sensitive device useful according to the first and second embodiments of this invention.

The above description of the first embodiment describes a moisture sensitive device having two comb electrodes on one side of the moisture sensitive element, but it has been found that this invention is also applicable to a moisture sensitive device wherein one comb electrode is placed on one side of the moisture sensitive element and the other comb electrode is on the other side, to a moisture sensitive device of the type shown in FIG. 2 which has two rectangular electrodes on the opposite sides of the moisture sensitive element, to a moisture sensitive device having two coil electrodes on one side of the moisture sensitive element as shown in FIG. 3, and to a moisture sensitive device having two coil electrodes on the opposite sides of the moisture sensitive element.

Figure 5:
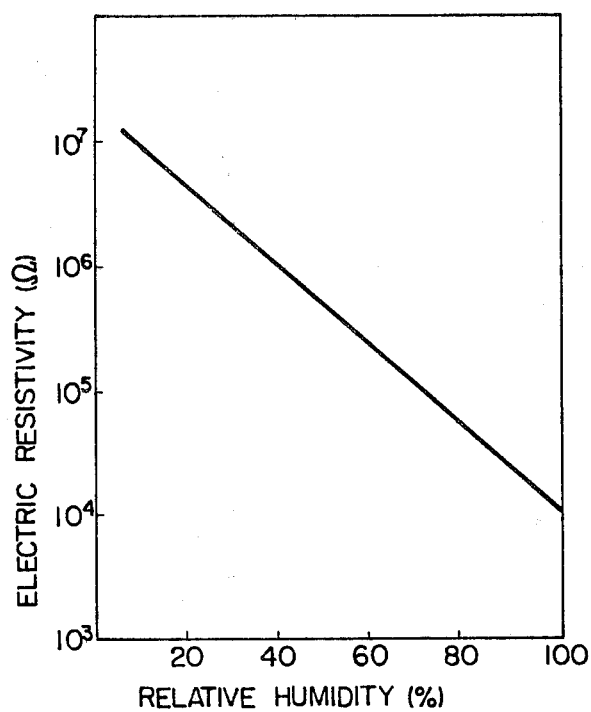
Figure 6:
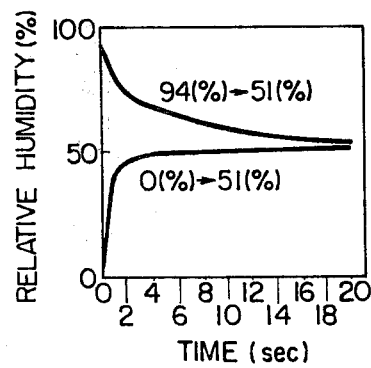
Figure 7:
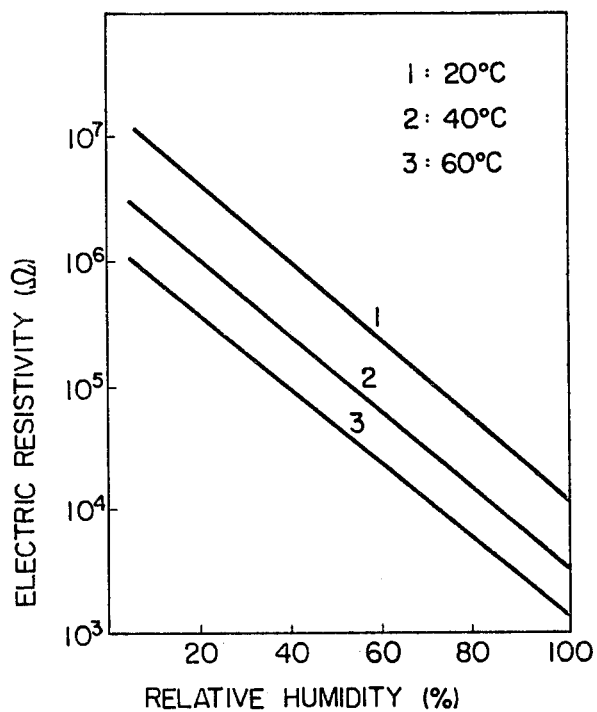
Figure 8:
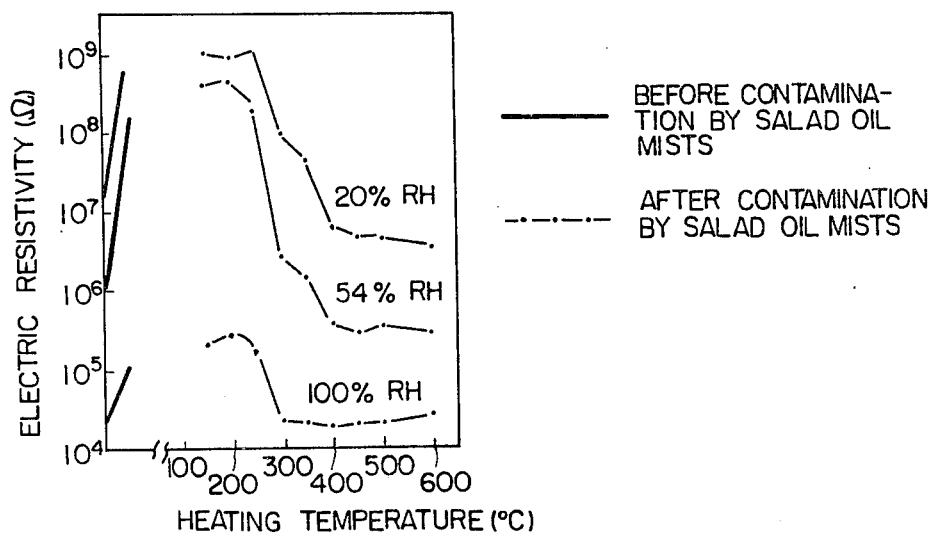
Figure 9:
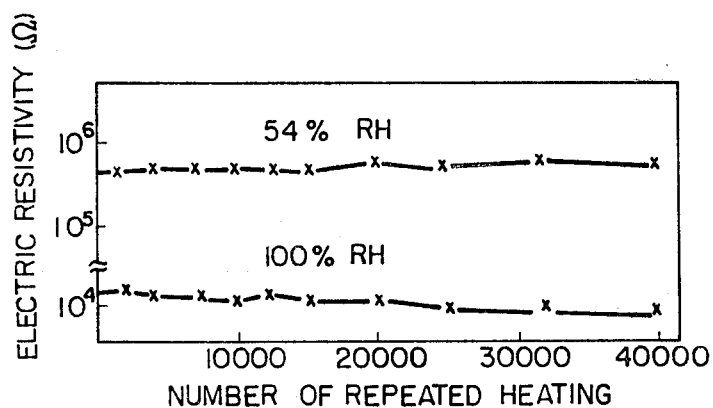

The moisture sensitive devices illustrated in FIGS. 2 and 3 can be produced by the general method described above used to produce the moisture sensitive device shown in FIG. 1, and their characteristics are substantially equal to those of the device shown in FIG. 1. The device having two rectangular electrodes on the opposite sides of the moisture sensitive element had the best relative humidity versus electrical resistivity characteristics (the characteristic curve of the device shown in FIG. 1 is depicted in FIG. 5). The first embodiment described above comprised a moisture sensitive element 1 made of $Ca_{10}(PO_4)_6(OH)_2$, but an element made of $Sr_{10}(PO_4)_6(OH)_2$, $Ba(PO_4)_6(OH)_2$ or a solid solution thereof can also be prepared by the same procedure from $MHPO_4$ and $MCO_3$, wherein M is at least one member selected from the group consisting of Ca, Sr and Ba. A moisture sensitive device of the design shown in FIGS. 1 to 3 can be produced by using the thus-prepared moisture sensitive element 1. It is confirmed by experiments that such devices have the same characteristics as those of the device using a moisture sensitive element made of $Ca_{10}(PO_4)_6(OH)_2$.

Figure 4:
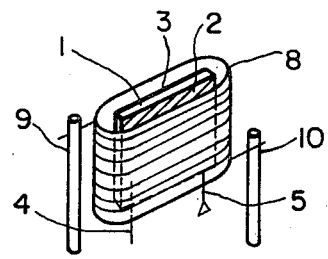
FIG. 4 is a perspective view showing the construction of another variation of a moisture sensitive device useful according to the first and second embodiments of this invention.

For cleaning purposes, these moisture sensitive devices should desirably have a heating means such as an electric heater. A very advantageous heating method is shown in FIG. 4 in which an integral or separate electric heater 8 is wound around the moisture sensitive device. The device shown in FIG. 4 has the same design as the one shown in FIG. 2 which has two rectangular electrodes formed on the opposite sides of the moisture sensitive element, but the heater 8 can also be wound around the other configurations of moisture sensitive device described above, and such devices have the same characteristics as those of the device shown in FIG. 4. In FIG. 4, the numerals 9 and 10 represent leads to the heater 8.

A second embodiment of this invention is now described by reference to FIGS. 1 to 4 and 11, and 12. As described above, the moisture sensitive device of this invention uses a moisture sensitive element 1 made of hydroxyapatite. To further reduce the electrical resistivity of the device for particular values of relative humidity, consideration was given to the possibility of replacing part of M in hydroxyapatite of $M_{10}(PO_4)_6(OH)_2$, wherein M is at least one member selected from the group consisting of Ca, Sr, and Ba by an alkali metal. It was already known from attempts to synthesize $M_{10}(PO_4)_6(OH)_2$ by coprecipitation that alkali ions such as $Na^+$ and $K^+$ formed a solid solution with $M_{10}(PO_4)(OH)_2$, and that $Ca_9Na(PO_4)_6F$ and $Ca_9Na(PO_4)_6Cl$ were present in fluoroapatite, respectively. Thinking that part of M in $M_{10}(PO_4)_6(OH)_2$ could be replaced by an alkali metal (A), it was attempted to produce a solid solution of the following formula:

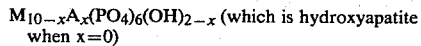
$M_{10-x}A_x(PO_4)_6(OH)_{2-x}$ (which is hydroxyapatite when x=0)

As starting materials, $CaHPO_4$ and $CaCO_3$ having a purity of more than 99.9% were measured in order to provide a composition of the formula $Ca_{10}(PO_4(OH)_2$, and the starting materials were thoroughly mixed in a ball mill. The mixture was put in a crucible and heated in an electric oven (using a known silico-unit heating element) in a steam atmosphere at 1000° C. for 10 hours. A powder X-ray photograph of the resulting ceramic composition showed that the $CaPO_4$ had reacted with the $CaCO_3$ to form the very stable hydroxyapatite $Ca_{10}(PO_4)(OH)_2$. That ceramic composition was ground to particles which were mixed with $Na_2CO_3$ particles in the molar ratios indicated in Table 1, and the respective mixtures were dispersed in an aqueous solution of polyvinyl alcohol in a mortar, and the resulting slurry was subsequently treated to provide a composition of granules of uniform size.

TABLE 1

| Sample No. | $Ca_{10}(PO_4)_6(OH)_2$ (mol %) | $Na_2CO_3$ (mol %) |
| --- | --- | --- |
| 10 | 100 | 0 |
| 20 | 90 | 10 |
| 30 | 80 | 20 |
| 40 | 70 | 30 |
| 50 | 40 | 60 |

The granules of each composition were pressed into a disc (25 mm in diameter × 3 mm thick) at a pressure of 700 kg/cm² using a press molding machine, and the disc was then fired in an electric oven in a steam atmosphere at from 1000° to 1200° C. for 5 hours. Each disc was then allowed to cool to room temperature. The thus-prepared ceramic disc was formed into a moisture sensitive element 1 as shown in FIG. 1. One side of the element was polished with an abrasive of mesh 800, and two comb-like patterns of gold paste were printed on the polished surface by a screen mesh method, and fired in the electric oven in air at 800° C. to provide of comb-shaped electrodes 2 and 3. The element was recovered from the oven and a moisture sensitive device was fabricated by soldering 90% platinum-rhodium leads 4 and 5 to the electrodes 2 and 3, respectively. By repeating this procedure, five moisture sensitive devices having different molar ratios of $Ca_{10}(PO_4)_6(OH)_4$ to $Na_2CO_3$ were fabricated. Particles of $Ba_{10}(PO_4)_6(OH)_2$ were also prepared in the same manner as used in preparing the particles of $Ca_{10}(PO_4)_6(OH)_2$. Then the particles were mixed with $K_2CO_3$ instead of $Na_2CO_3$ in the molar ratios indicated in Table 2 below, and by analogously repeating the procedure that was for the production of the moisture sensitive devices using $Na_2CO_3$, another group of moisture sensitive devices of the construction shown in FIG. 1 having different molar ratios of $Ba_{10}(PO_4)_6(OH)_2$ to $K_2CO_3$ were fabricated.

TABLE 2

| Sample No. | $Ba_{10}(PO_4)_6(OH)_2$ (mol %) | $K_2CO_3$ (mol %) |
| --- | --- | --- |
| 110 | 100 | 0 |
| 120 | 90 | 10 |
| 130 | 80 | 20 |
| 140 | 70 | 30 |
| 150 | 40 | 60 |

Figure 11:
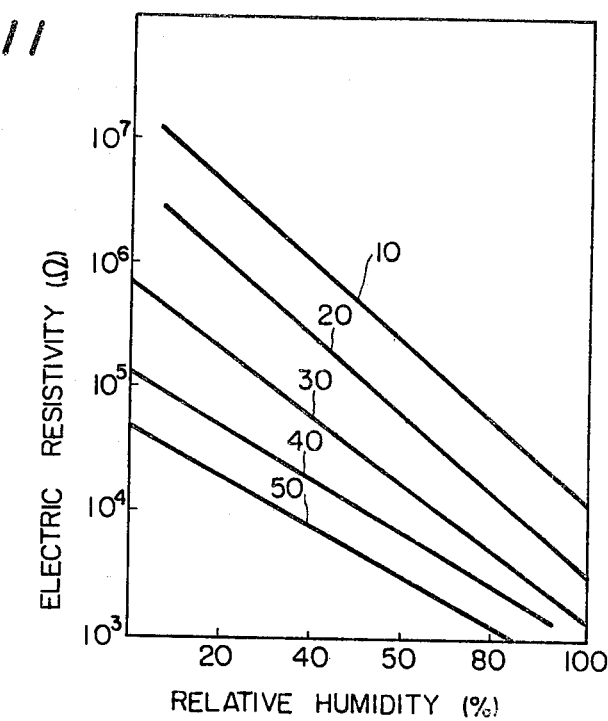
FIG. 11 is a diagram showing the relative humidity versus electrical resistivity profile of the moisture sensitive device according to a second embodiment of this invention.
Figure 12:
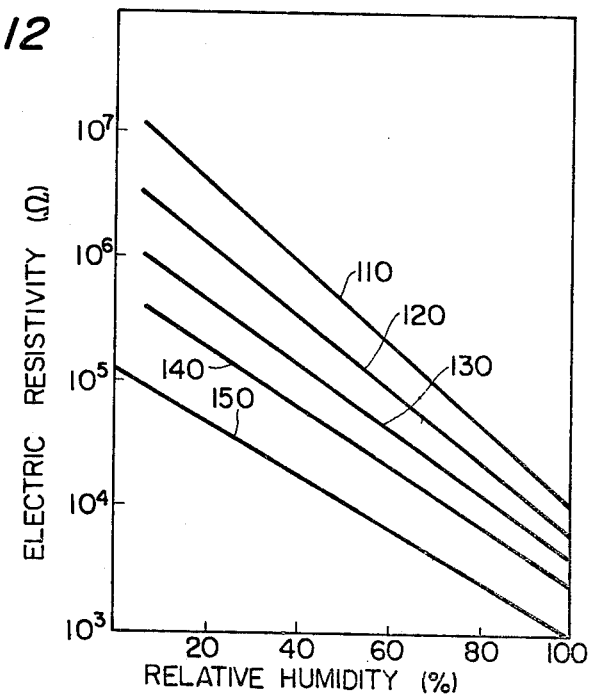
FIG. 12 is a diagram showing the relative humidity versus electrical resistivity profile of a moisture sensitive device according to a second embodiment of this invention using a different moisture sensitive element from that used in the device having the characteristic curve depicted in FIG. 11.
Figure 13:
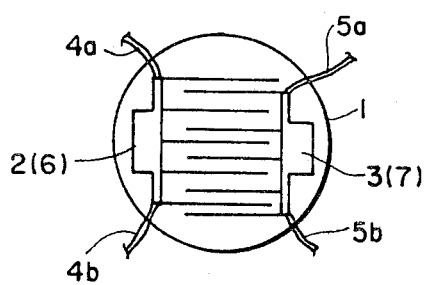
FIG. 13 is a schematic view showing the construction of a moisture sensitive device according to a third embodiment of this invention, described hereinafter.

An ohmmeter was connected between the leads 4 and 5 of each device, and the resistivity across the comb electrodes 2 and 3 was measured by varying the relative humidity in a range of from 0 to 100% at 20° C. The results are depicted by relative humidity versus electrical resistivity curves shown in FIGS. 11 and 12. The curve in FIG. 11 represents the characteristics of the moisture sensitive element made of $Ca_{10}(PO_4)_6(OH)_2$ and $Na_2CO_3$, and that in FIG. 12 represents the characteristics of the moisture sensitive element made of Ba$_{10}$-(PO$_4$)$_6$(OH)$_2$ and K$_2$CO$_3$. As can be seen from these figures, the moisture sensitive device using a moisture sensitive element 1, made of the combination of M$_{10}$(PO$_4$)$_6$(OH)$_2$ (wherein M is at least one member selected from the group consisting of Sr, Ca and Ba) and Na$_2$CO$_3$ or K$_2$CO$_3$ exhibits electrical resistivity for a given relative humidity significantly lower than the device using a moisture sensitive element made of M$_{10}$(PO$_4$)$_6$(OH)$_2$ alone, and the combination of M$_{10}$(PO$_4$)$_6$(OH)$_2$ and Na$_2$CO$_3$ in a given molar ratio generally has a lower electrical resistivity for a given relative humidity than the combination with K$_2$CO$_3$ having the same molar ratio. It can also be seen that either combination provides a relative humidity versus electrical resistivity profile which is substantially linear over the entire RH range of from 0 to 100% and assures accurate measurement of a wide range of RH. As is also clear from FIGS. 11 and 12, the more Na$_2$CO$_3$ or K$_2$CO$_3$ that is mixed with M$_{10}$(PO$_4$)$_6$(OH)$_2$, the lower the resistivity for a given relative humidity.

However, if the content of alkali metal carbonate exceeds 60%, the device becomes less sensitive to moisture and cannot achieve the desired object. Therefore, for the purposes of this invention, the amount of Na$_2$CO$_3$ and K$_2$CO$_3$ added to M$_{10}$(PO$_4$)$_6$(OH)$_2$ should not be more than 60 mol %.

The temperature dependency resistance to contaminats, resistance to repeated heating, and time-dependent change in sensitivity of the moisture sensitive devices prepared from a moisture sensitive element made of M$_{10}$(PO$_4$)$_6$(OH)$_2$ combined with less than 60 mol % of Na$_2$CO$_3$ or K$_2$CO$_3$ were also examined, and the results were substantially the same as those obtained with the moisture sensitive device using a moisture sensitive element 1 made of M$_{10}$(PO$_4$)$_6$(OH)$_2$ alone.

Based on these findings, it was confirmed that part of the M in M$_{10}$(PO$_4$)$_6$(OH)$_2$ can be replaced by an alkali metal, such as Na and K, as represented by the following chemical equation:

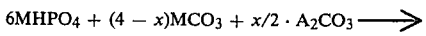

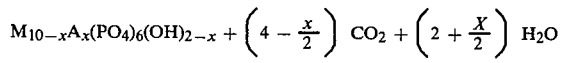

(wherein A represents an alkali metal).

From the above chemical equation it is apparent that the amount of A in A$_2$CO$_3$ used as a starting material is the same as that of A contained in the product and therefore the molar amount of A$_2$CO$_3$ is equivalent to that of A in the product expressed in terms of A$_2$O.

It was also found that the moisture sensitive device using a moisture sensitive element made of a compound identified above could be cleaned of contaminants by heating to about 450° C., but for this cleaning purpose, the device must be heated to a temperature no higher than about 450° C. and the temperature thereof detected with a thermistor or other suitable temperature sensitive element. Therefore an examination was made to determine if the moisture sensitive element made of the compound identified above might have the function of a thermistor or the like, because if it had this function, no separate thermistor or a like component need be incorporated in the moisture sensitive device. As a result, it was found that said element did have the function of a thermistor at a temperature higher than about 100° C.

The moisture sensitive device according to the second embodiment of this invention, like the device according to the first embodiment, uses an electric heater or other heating means for cleaning purposes, and as shown in FIG. 4, an integral or separate electric heater 8 may be wound around the device.

As described above, the moisture sensitive device according to the second embodiment of this invention has all the advantages of the device according to the first embodiment that uses a moisture sensitive element made of hydroxyapatite of the formula M$_{10}$(PO$_4$)$_6$(OH)$_2$. In addition, the device of the second embodiment provides electrical resistivities significantly lower than those of the device of the first embodiment, and can function as a thermistor upon heating to 100° C.

In the second embodiment described above, the starting material was CaHPO$_4$ and CaCO$_3$ having a purity of more than 99.9%, but a starting material of lower purity can be used if the impurities that it contains so permit. Studies have also revealed that the material for the moisture sensitive element 1 can also be prepared by synthesis in an aqueous solution or any other method well known in the ceramic industry.

The above description of the second embodiment described a moisture sensitive device having two comb electrodes on one side of the moisture sensitive element, but it has been found that this invention is also applicable to a moisture sensitive device wherein one comb electrode is placed on one side of the moisture sensitive element and the other comb electrode is placed on the other side, to a moisture sensitive device of the type shown in FIG. 2 which has two rectangular electrodes on the opposite sides of the moisture sensitive element, to a moisture sensitive device having two coil electrodes on one side of the moisture sensitive element as shown in FIG. 3, and to a moisture sensitive device having two coil electrodes on the opposite sides of the moisture sensitive element (not shown).

The moisture sensitive devices illustrated in FIGS. 2 and 3 can be produced by the method used to produce the moisture sensitive device shown in FIG. 1, and their characteristics are similar to those of the device of FIG. 1 which are depicted in FIGS. 11 and 12. The device having two rectangular electrodes on the opposite sides of the moisture sensitive element had the best relative humidity versus electrical resistivity characteristics (the characteristic curves of the device shown in FIG. 1 are depicted in FIGS. 11 and 12.

The above description of the second embodiment also described a moisture sensitive element 1 made of the combination of M$_{10}$(PO$_4$)$_6$(OH)$_2$ with Na$_2$CO$_3$ or K$_2$CO$_3$, but since part of M in M$_{10}$(PO$_4$)$_6$(OH)$_2$ can be replaced by Na or K, part of M was replaced by other alkali metals in the molar ratios indicated in Tables 1 and 2, and it was found that the resulting moisture sensitive elements had similar characteristics. To achieve the desired effect, the alkali metals other than Na and K also had to be used in an amount of less than 60 mol %. It was also found that the combination of M$_{10}$(PO$_4$)$_6$(OH)$_2$ with Na$_2$CO$_3$ in a given molar ratio had a lower electrical resistivity for a given relative humidity than any other combination having the same molar ratio.

A moisture sensitive device according to a third embodiment of this invention is now described by reference to FIGS. 13 to 16. As described in the foregoing pages, it was found that a moisture sensitive device having the good characteristics described above can be produced by preparing a moisture sensitive element 1 from hydroxyapatite. When the surface of this device is contaminated by foreign matter, it provides a different electrical resistivity for a given relative humidity, so it must be cleaned of such contaminant by heating to about 450° C. for restoring the initial characteristics. To this end, an electric heater or other means for heating the device to about 450° C. is necessary, but if heaters 6 and 7 separate from the electrodes 2 and 3 are wound around the moisture sensitive element 1, the moisture sensitive device necessitates a large space requirement, and installing the electrodes 2 and 3 and heaters 6 and 7 separately adds to the number of steps for fabricating the device. Therefore, efforts were made to eliminate the need of using a separate heater, and it was found that a moisture sensitive device having the construction described below made such heater unnecessary.

Therefore, a device according to the third embodiment of this invention comprises a moisture sensitive element 1 that was prepared from hydroxyapatite by the procedure described above and which had, on one of its sides, electrodes 2 and 3 that also served as heaters 6 and 7. More specifically, a moisture sensitive element 1 was prepared from hydroxyapatite by the procedure described above, but instead of gold paste, two comb-like patterns of a RuO-base paste were printed on one surface of the element by a screen mesh method, and the element was fired in an electric oven in air at 800° C. to form electrodes 2 and 3, which also served as heaters 6 and 7. We then soldered two 90% platinum-rhodium electrical leads (hereinafter "leads") to each electrode, a first group of leads 4a and 4b being connected to the electrode 2 and a second group of leads 5a and 5b being connected to the electrode 3. Relative humidity can be measured with this type of device by the following procedure: an ohmmeter is connected between either one of the first group of leads 4a and 4b and either one of the second group of leads 5a and 5b to measure the electrical resistance across the electrodes 2 and 3; then the measured value of electrical resistivity is checked against the reference electrical resistivity versus relative humidity curve to determine the relative humidity. If the moisture sensitive device deteriorates because of age or a hostile environment, either one of the leads 4a and 4b of the first group can be connected with either one of the leads 5a and 5b of the second group, and voltage applied between the other leads of the first and second groups to obtain a current flow between the two electrodes 2 and 3. Then, the electrodes 2 and 3 work as heaters 6 and 7 that heat the moisture sensitive element 1 to restore the initial moisture sensitivity of the element. Heat equivalent to a power of from several watts to several tens of watts is required for the heaters 6 and 7 to achieve the desired effect, but then the heaters must have an electrical resistance of at least about 50 to 55 ohms for a supply of 10 volts. However, since the moisture sensitive element 1 made of hydroxyapatite has a resistivity of at least $10^3$ ohms, the required resistivity of the electrodes stated above poses no problem at all in measuring electrical resistivity with the element 1.

Figure 14:
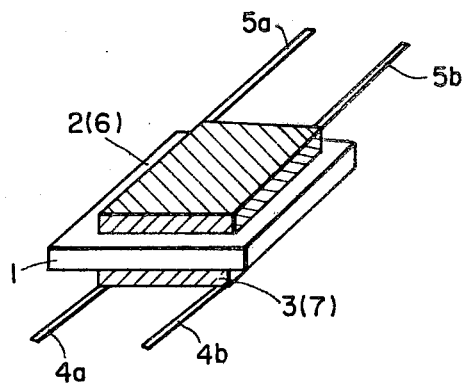
FIG. 14 is a perspective view showing the construction of another moisture sensitive device according to the third embodiment of this invention.
Figure 15:
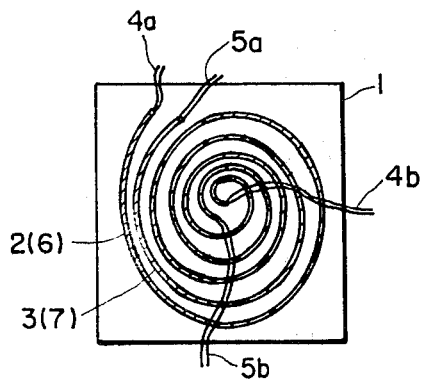
FIG. 15 is a plan view showing the construction of still another moisture sensitive device according to the third embodiment of this invention.
Figure 16:
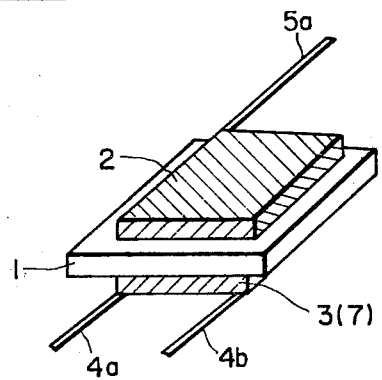
FIG. 16 is a plan view showing the construction of another further variation of a moisture sensitive device according to the third embodiment of this invention.

The above description of the third embodiment of this invention describes a moisture sensitive device having two comb electrodes on one side of the moisture sensitive element, but it has been found that this invention is also applicable to a moisture sensitive device wherein one comb electrode is placed on one side of the moisture sensitive element and the other comb electrode is on the other side, to a moisture sensitive device of the type shown in FIG. 14 which has two rectangular electrodes on the opposite sides of the moisture sensitive element, to a moisture sensitive device having two coil electrodes on one side of the moisture sensitive element as shown in FIG. 15, and to a moisture sensitive device having two coil electrodes on the opposite sides of the moisture sensitive element. Similar moisture sensitivity is exhibited by these modifications. The above description of the third embodiment also describes the use of both electrodes 2 and 3 as heaters 6 and 7, but as shown in FIG. 16, only the one electrode, e.g., 3, may be used as a heater. In this case, two leads 4a and 4b are connected to the electrode 3 and only one lead 5a is connected to the other electrode 2, and then a current is applied through the leads 4a.

FIG. 16 is directed to the case where only one of the electrodes 2 and 3 of a moisture sensitive device equivalent to the device of FIG. 14 which has two rectangular electrodes on the opposite sides of the moisture sensitive element is used as heater, but the concept of FIG. 16 can also be applied to the four general structural variations described above without causing any drop in moisture sensitivity. In addition, the above description has assumed the use of RuO-base paste as a material for the electrodes 2 and 3 which also serve as heaters 6 and 7, but any material having electrical properties equal to those of RuO may be used.

As described in the foregoing description, the moisture sensitive device according to the first embodiment of this invention is characterized by using a moisture sensitive element 1 made of $M_{10}(PO_4)_6(OH)_2$ (wherein M is at least one member selected from the group consisting of Sr, Ca and Ba) and achieves the following advantages:

(1) its moisture sensitivity varies little with time after heating;
(2) it exhibits an electrical resistivity that varies greatly with a change in relative humidity;
(3) because it is stable at elevated temperatures, it can be cleaned of surface contaminants simply by heating, and this way, its initial moisture sensitivity can be easily restored;
(4) because it is made of a single component, products having fairly consistent characteristics can be produced;
(5) it has a short response time;
(6) it is resistant to contaminants and repeated heating;
(7) its characteristics after cleaning by heating are stable for an extended period of time; and
(8) it offers an industrially advantageous product that can be produced from a cheap material by a simple method known in the ceramic industry.

The moisture device according to the second embodiment of this invention is characterized by using a moisture sensitive element 1 comprising 100 to 40 mol % of a compound having the formula $M_{10}(PO_4)_6(OH)_2$ (wherein M is at least one member selected from the group consisting of Sr, Ca and Ba) and 0 to 60 mol % of an alkali metal (to be represented by A) in terms of $M_{10}(PO_4)_6(OH)_2$ and $A_2O$, respectively, and the device has, in addition to the above-described eight advantages of the device of the first embodiment, the following two advantages:

(9) its electrical resistivity for a given relative humidity is lower than that of the device of the first embodiment; and

(10) it can be used as a thermistor at 100° C. or higher.

The moisture device according to the third embodiment of this invention is equal to the device according to the first or second embodiment except that the electrodes 2 and 3 on the moisture sensitive element 1 also serve as heaters 6 and 7. The resulting advantages are the production of a low cost device that is smaller in size and which can be fabricated through fewer steps, and these advantages are in addition to advantages (1) to (8) when the device uses the moisture sensitive element 1 according to the first embodiment, and to advantages (1) to (10) when the device uses the moisture sensitive element 1 according to the second embodiment.

While the invention has been described in detail and with reference to specific embodiments thereof, it will be apparent to one skilled in the art that various changes and modifications can be made therein without departing from the spirit and scope thereof.

What is claimed is:

1. A moisture sensitive device comprising a moisture sensitive element including a material comprising $M_{10}(PO_4)_6(OH)_2$, wherein M is at least one member selected from the group consisting of Sr, Ca and Ba, at least two electrodes formed on said moisture sensitive element, with said electrodes being separated by said element, and to each of said electrodes is connected at least one electrical lead.

2. A moisture sensitive device according to claim 1 wherein said moisture sensitive element includes a material comprising from 100 to about 40 mol % of a compound having the formula $M_{10}(PO_4)_6(OH)_2$, wherein M is at least one member selected from the group consisting of Sr, Ca and Ba, and from 0 to about 60 mol % of an alkali metal denoted by A, the molar amounts being calculated as $M_{10}(PO_4)_6(OH)_2$ and $A_2O$, respectively.

3. A moisture sensitive device according to claim 2 wherein said alkali metal is sodium.

4. A moisture sensitive device according to claim 1 or 2 wherein said moisture sensitive device comprises a means for heating the moisture sensitive element.

5. A moisture sensitive device according to claim 4 wherein at least one of said electrodes also serves as a means for heating the moisture sensitive element.

6. A moisture sensitive device according to claim 5 wherein said heating means is capable of heating the moisture sensitive element to at least about 450° C.

7. A moisture sensitive device according to claim 5 wherein every electrode serving as heating means is made of a material comprising RuO.

8. A moisture sensitive device according to claim 5 wherein at least two leads are connected to said at least one electrode serving as heating means.

9. A moisture sensitive device according to claim 1 or 2 wherein the moisture sensitive element is in a sheet form and the electrodes are a pair of like-shaped electrodes which are formed on one side of the moisture sensitive element.

10. A moisture sensitive device according to claim 1 or 2 wherein the moisture sensitive element is in a sheet form and the electrodes are a pair of like-shaped electrodes one of which is formed on one side of the element and the other of which is formed on the other side of the element.

11. A moisture sensitive device according to claim 10 wherein the electrodes are rectangular.

12. A moisture sensitive device according to claim 5 wherein the moisture sensitive element is in a sheet form and the electrodes are a pair of like-shaped electrodes which are formed on one side of the moisture sensitive element.

13. A moisture sensitive device according to claim 5 wherein the moisture sensitive element is in a sheet form and the electrodes are a pair of like-shaped electrodes one of which is formed on one side of the element and the other of which is formed on the other side of the element.

14. A moisture sensitive device according to claim 13 wherein the electrodes are rectangular.

15. A moisture sensitive device according to claim 4 comprising a heating means wound around the moisture sensitive element.

* * * * *